(12) United States Patent
Chen et al.

(10) Patent No.: US 11,937,901 B2
(45) Date of Patent: Mar. 26, 2024

(54) ARTERIOVENOUS FISTULA STENOSIS DETECTION SYSTEM AND METHOD THEREOF AND SENSING DEVICE

(71) Applicant: Above Care Inc., San Jose, CA (US)

(72) Inventors: Wei-Ta Chen, Taipei (TW); Yung-Hsin Chen, San Jose, CA (US)

(73) Assignee: Above Care Inc., San Jose, CA (US)

( * ) Notice: Subject to any disclaimer, the term of this patent is extended or adjusted under 35 U.S.C. 154(b) by 827 days.

(21) Appl. No.: 16/388,888

(22) Filed: Apr. 19, 2019

(65) Prior Publication Data
US 2019/0320912 A1    Oct. 24, 2019

Related U.S. Application Data

(60) Provisional application No. 62/660,944, filed on Apr. 21, 2018.

(51) Int. Cl.
| | |
|---|---|
| *A61B 5/02* | (2006.01) |
| *A61B 5/026* | (2006.01) |
| *A61B 7/02* | (2006.01) |
| *G16H 50/20* | (2018.01) |
| *G16H 50/30* | (2018.01) |

(52) U.S. Cl.
CPC .......... *A61B 5/02007* (2013.01); *A61B 5/026* (2013.01); *A61B 7/02* (2013.01); *G16H 50/20* (2018.01); *G16H 50/30* (2018.01)

(58) Field of Classification Search
CPC .. A61B 5/02007; A61B 5/7267; G16H 50/20; G16H 50/30
See application file for complete search history.

(56) References Cited

U.S. PATENT DOCUMENTS

| | | | | |
|---|---|---|---|---|
| 2006/0245597 | A1* | 11/2006 | Guion-Johnson | A61B 7/04 381/67 |
| 2015/0366530 | A1* | 12/2015 | Ku | A61B 5/02 600/483 |
| 2017/0014033 | A1* | 1/2017 | Koo | G16H 50/30 |
| 2017/0018081 | A1* | 1/2017 | Taylor | A61B 6/504 |

FOREIGN PATENT DOCUMENTS

| | | |
|---|---|---|
| TW | 201600068 | 1/2016 |
| TW | 201740369 | 11/2017 |

\* cited by examiner

*Primary Examiner* — Carrie R Dorna
*Assistant Examiner* — Karen E Toth
(74) *Attorney, Agent, or Firm* — JCIP GLOBAL INC.

(57) ABSTRACT

An arteriovenous fistula (AVF) stenosis detection system and method thereof and sensing device are provided. The AVF stenosis detection system includes: a sensing device including a microphone; and a server coupled to the sensing device. The sensing device contacts a first location of a patient body, wherein there is a first distance between the first location and a second location of an AVF of the patient body, and the first location is located on an extended path of an artery or a vein corresponding to the AVF. The sensing device receives a frequency spectrum signal through the microphone and transmits the frequency spectrum signal to the server. The server calculates a stenosis percentage of the AVF corresponding to the frequency spectrum signal through a machine learning module and transmits the stenosis percentage to the sensing device.

7 Claims, 5 Drawing Sheets

ARTERIOVENOUS FISTULA STENOSIS DETECTION SYSTEM AND METHOD THEREOF AND SENSING DEVICE

CROSS-REFERENCE TO RELATED APPLICATION

This application claims the priority benefit of U.S. provisional application No. 62/660,944, filed on Apr. 21, 2018. The entirety of the above-mentioned patent application is hereby incorporated by reference herein and made a part of this specification.

BACKGROUND

Technical Field

The invention relates to an Arteriovenous Fistula (AVF) stenosis detection system and a method thereof and a sensing device, and particularly relates to an AVF stenosis detection system adapted to detect a stenosis percentage of an AVF and a method thereof and a sensing device.

Description of Related Art

Arteriovenous Fistula (AVF) is a connection between an artery and a vein, and is produced by a surgeon. Stenosis an abnormal narrowed state of an AVF passage, which is a main cause of AVF dysfunction. In the current practice, doctors evaluate a condition of the AVF every month or every two or three months. However, the AVF stenosis may occur in weeks or even days. Therefore, to quickly and conveniently evaluate the stenosis condition of the AVF is a goal of those skilled in the art in this field.

SUMMARY

The invention is directed to an Arteriovenous Fistula (AVF) stenosis detection system and a method thereof and a sensing device, which are adapted to quickly and conveniently evaluate a stenosis condition of an AVF.

The invention provides an AVF stenosis detection system including a sensing device including a microphone; and a server coupled to the sensing device. The sensing device contacts a first location of a patient body, wherein there is a first distance between the first location and a second location of an AVF of the patient body, and the first location is located on an extended path of an artery or a vein corresponding to the AVF. The sensing device receives a frequency spectrum signal through the microphone and transmits the frequency spectrum signal to the server. The server calculates a stenosis percentage of the AVF corresponding to the frequency spectrum signal through a machine learning module and transmits the stenosis percentage to the sensing device.

In an embodiment of the invention, the machine learning module performs a training operation by using the frequency spectrum signal corresponding to a plurality of different first locations, and calculates the stenosis percentage according to a result of the training operation.

In an embodiment of the invention, the server receives angiography information of the patient body and determines a real stenosis percentage according to the angiography information, and the machine learning module trains a plurality of parameters according to the real stenosis percentage to correct the stenosis percentage.

In an embodiment of the invention, the microphone is coupled to a confined space of the sensing device.

In an embodiment of the invention, the machine learning module calculates the stenosis percentage according to a plurality of parameters, and the parameters include at least one of age information, gender information, blood pressure information, left or right hand, patient historic data, and big data of the server.

The invention provides a method for detecting AVF stenosis, which includes: using a sensing device to contact a first location of a patient body, wherein there is a first distance between the first location and a second location of an AVF of the patient body, and the first location is located on an extended path of an artery or a vein corresponding to the AVF; using the sensing device to receive a frequency spectrum signal through a microphone and transmitting the frequency spectrum signal to a server; and using the server to calculate a stenosis percentage of the AVF corresponding to the frequency spectrum signal through a machine learning module and transmitting the stenosis percentage to the sensing device.

In an embodiment of the invention, the machine learning module performs a training operation by using the frequency spectrum signal corresponding to a plurality of different first locations, and calculates the stenosis percentage according to a result of the training operation.

In an embodiment of the invention, the server receives angiography information of the patient body and determines a real stenosis percentage according to the angiography information, and the machine learning module trains a plurality of parameters according to the real stenosis percentage to correct the stenosis percentage.

In an embodiment of the invention, the microphone is coupled to a confined space of the sensing device.

In an embodiment of the invention, the machine learning module calculates the stenosis percentage according to a plurality of parameters, and the parameters include at least one of age information, gender information, blood pressure information, left or right hand, patient historic data, and big data of the server.

The invention provides a sensing device coupled to a server. The sensing device includes a microphone. The sensing device contacts a first location of a patient body, wherein there is a first distance between the first location and a second location of an AVF of the patient body, and the first location is located on an extended path of an artery or a vein corresponding to the AVF. The sensing device receives a frequency spectrum signal through the microphone and transmits the frequency spectrum signal to the server. The server calculates a stenosis percentage of the AVF corresponding to the frequency spectrum signal through a machine learning module and transmits the stenosis percentage to the sensing device.

Based on the above description, in the AVF stenosis detection system, the method thereof and the sensing device of the invention, the sensing device contacts any location on the extended path of the artery or the vein corresponding to the AVF to receive the frequency spectrum signal and transmits the frequency spectrum signal to the server. The server calculates the stenosis percentage of the AVF corresponding to the frequency spectrum signal and transmits the stenosis percentage to the sensing device.

To make the aforementioned more comprehensible, several embodiments accompanied with drawings are described in detail as follows.

BRIEF DESCRIPTION OF THE DRAWINGS

The accompanying drawings are included to provide a further understanding of the invention, and are incorporated

DESCRIPTION OF THE EMBODIMENTS

Figure 1:
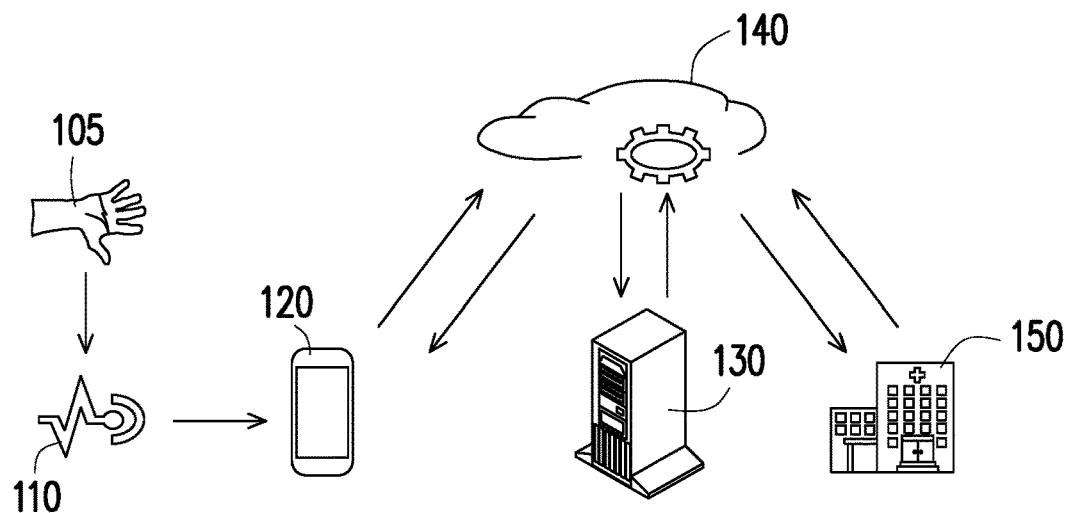
FIG. 1 is a block diagram of an Arteriovenous Fistula (AVF) stenosis detection system according to an embodiment of the invention.

FIG. 1 is a block diagram of an Arteriovenous Fistula (AVF) stenosis detection system according to an embodiment of the invention.

Referring to FIG. 1, the AVF stenosis detection system 100 of an embodiment of the invention includes a sensing device 110, a mobile device 120 and a server 130. The sensing device 110 obtains physiological data from a patient body 105 and transmits the physiological data to the mobile device 120 by using a wireless communication protocol such as WiFi or Bluetooth, etc. The mobile device 120 transmits the physiological data to the server 130 through a wireless network 140 by using a wireless communication protocol such as 4G or 5G, etc. The server 130 may analyze the physiological data through a machine learning module, and transmit back an analysis result to the mobile device 120 to display. Moreover, the server 130 may further transmit the analysis result to a medical organization 150 through the wireless network 140 for patient condition management.

In the embodiment, although a situation that the sensing device 110 is communicated with the server 130 through the mobile device 120 is described, the invention is not limited thereto. In another embodiment, a plurality of sensing devices 110 may also construct an Internet of Things (IOT) network, and may directly communicate with the server 130 through the IOT network. The sensing device 110 may directly transmit the physiological data to the server 130 and obtain the analysis result from the server 130 for displaying on the sensing device 110.

Figure 2A:
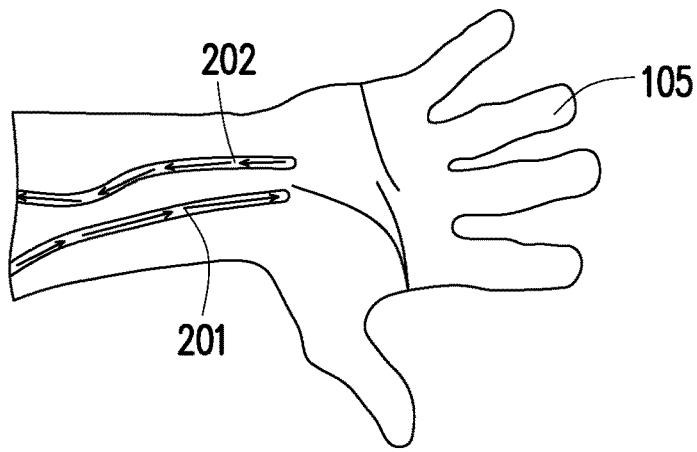
FIG. 2A is a schematic diagram of an artery and a vein before surgery according to an embodiment of the invention.
Figure 2B:
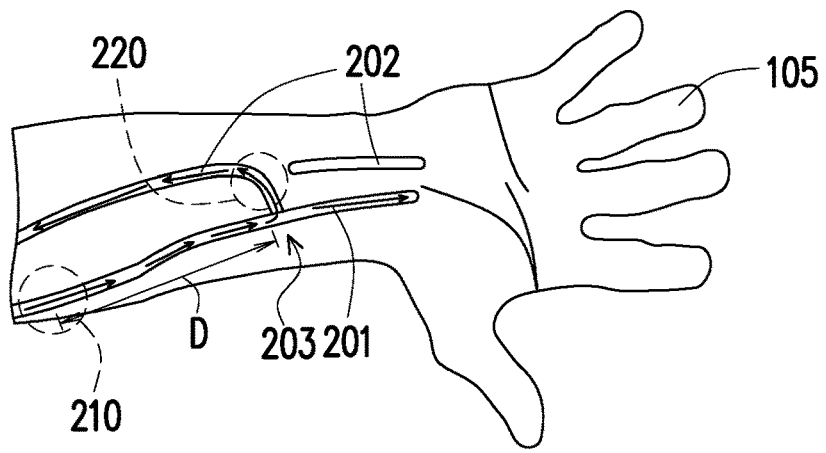
FIG. 2B is a schematic diagram of the artery, the vein and an AVF after the surgery according to an embodiment of the invention.

FIG. 2A is a schematic diagram of an artery and a vein before surgery according to an embodiment of the invention. FIG. 2B is a schematic diagram of the artery, the vein and an AVF after the surgery according to an embodiment of the invention.

Referring to FIG. 2A and FIG. 2B, FIG. 2A illustrates an artery 201 and a vein 202 of the patient body 105 before surgery. FIG. 2B illustrates the artery 201, the vein 202 and an AVF 203 connecting the artery 201 and the vein 202 of the patient body 105 after the surgery. In the embodiment, the AVF 203 is located on an arm of the patient body 105, though the invention is not limited thereto. In another embodiment, the AVF 203 may also be located at any part of the patient body 105.

Figure 3A:
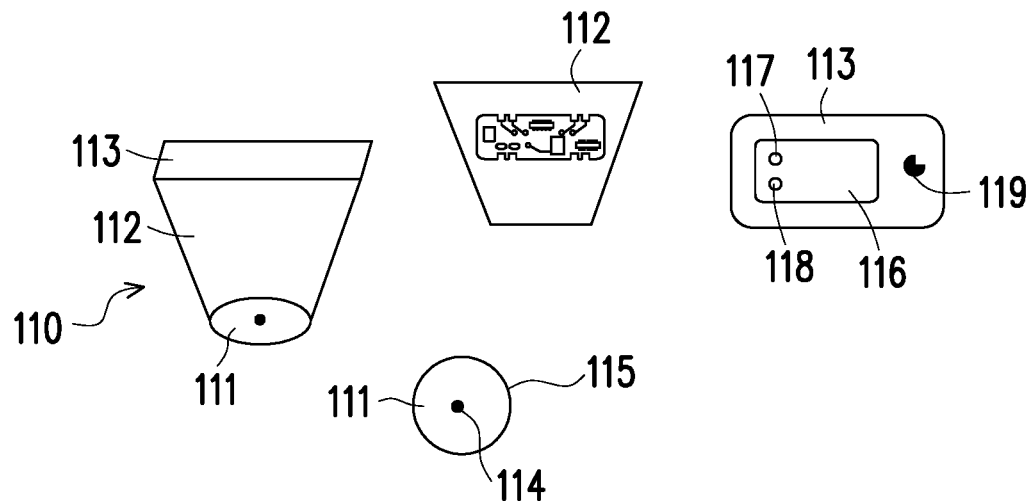
FIG. 3A is a schematic diagram of a sensing device according to an embodiment of the invention.
Figure 3B:
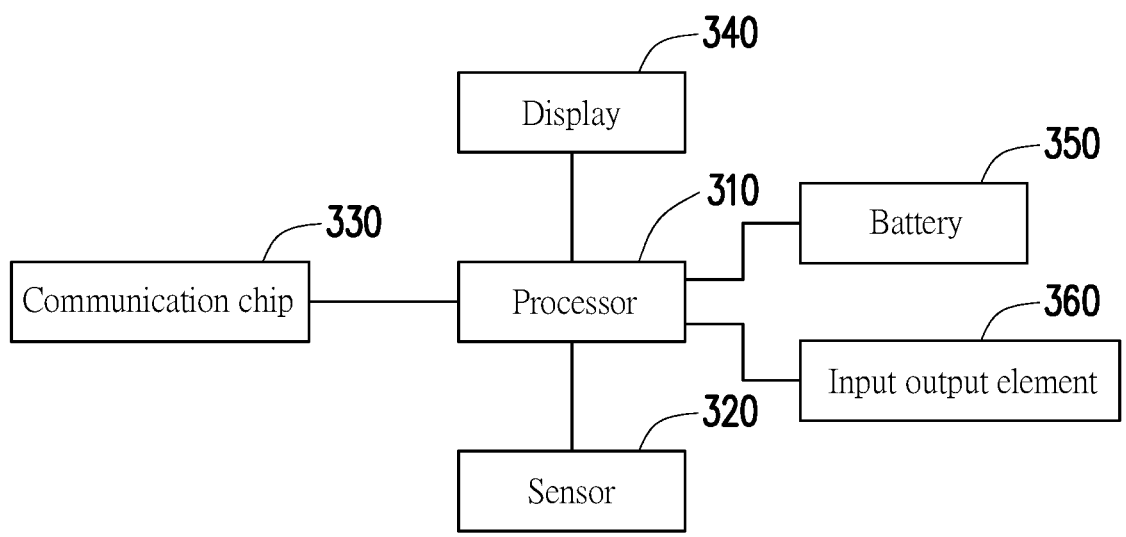
FIG. 3B is a block diagram of the sensing device according to an embodiment of the invention.
Figure 4A:
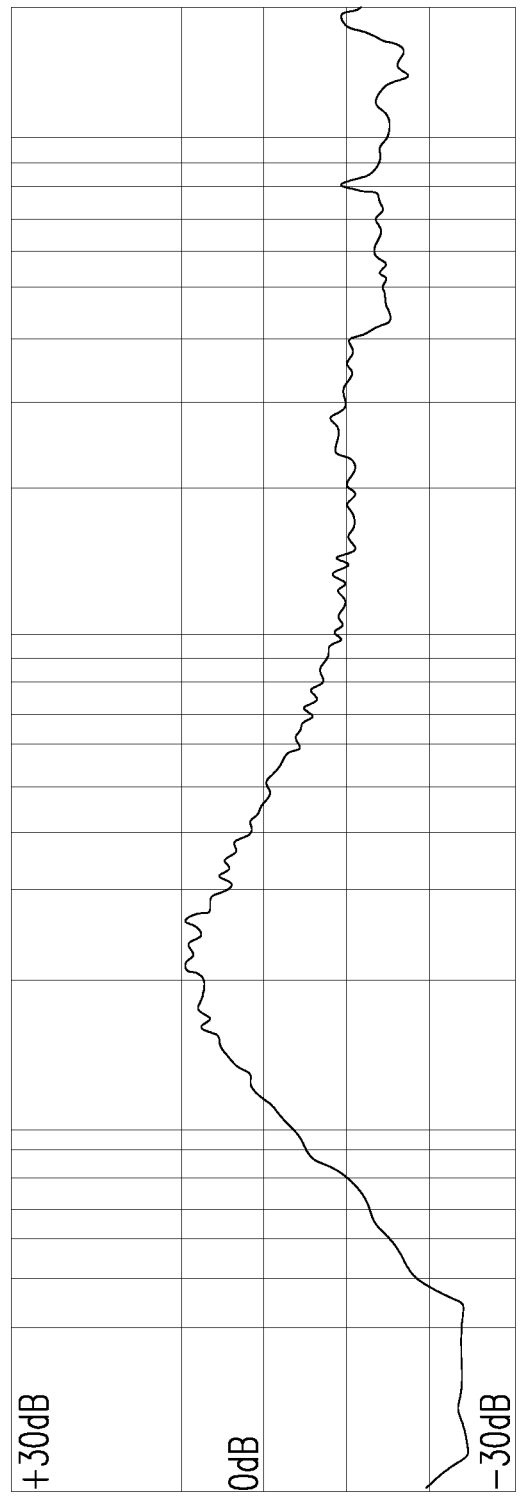
FIG. 4A is a frequency spectrum signal of an AVF without a stenosis condition according to an embodiment of the invention.
Figure 4B:
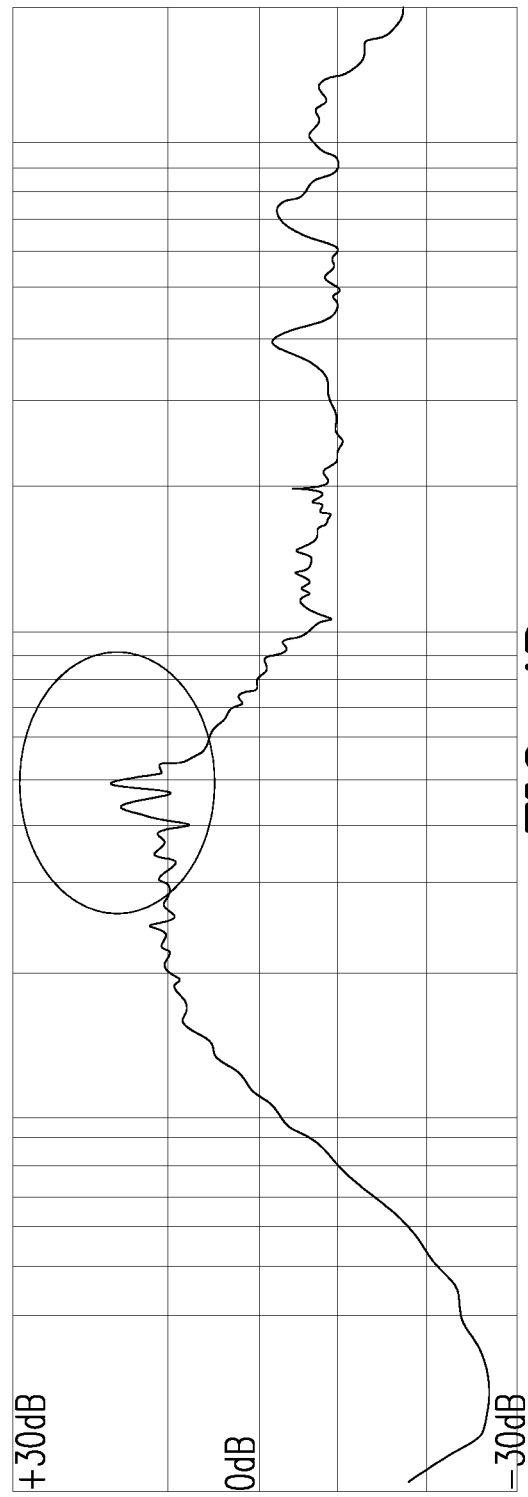
FIG. 4B is a frequency spectrum signal of an AVF with a severe stenosis condition according to an embodiment of the invention.3

FIG. 3A is a schematic diagram of a sensing device according to an embodiment of the invention. FIG. 3B is a block diagram of the sensing device according to an embodiment of the invention. FIG. 4A is a frequency spectrum signal of the AVF without a stenosis condition according to an embodiment of the invention. FIG. 4B is a frequency spectrum signal of the AVF with a severe stenosis condition according to an embodiment of the invention.

Referring to FIG. 3A, the sensing device 110 of an embodiment of the invention may include a first portion 111, a second portion 112 and a third portion 113. The first portion 111 may include a microphone 114 and a soft cushion ring 115. Through a construction of the first portion 111, the sensing device 110 may comfortably contact the patient's skin. The second portion 112 may include a circuit structure. The third portion 113 may include a display 116, a power Light-Emitting Diode (LED) 117, a transmission LED 118 and a charging port 119. The display 116 may display an analysis result indicating whether the AVF is stenosing, for example, a stenosis percentage. It should be noted that the microphone 114 may also be coupled to a confined space of the second portion 112 to reduce a noise generated when the physiological data is obtained. The microphone 114 may include an audio transducer and obtain the physiological data reflected by the patient body 105. Similarly, when the soft cushion ring 115 is closely attached to the patient's skin, the first portion 111 and the patient's skin also form a confined space, so that when the microphone obtains the physiological data, the noise is reduced. The soft cushion ring 115 may include a foamed cotton material without chemical material. The power LED 117 may have different light-emitting modes according to whether the sensing device 110 is in operation or not. The transmission LED 118 may have different light-emitting modes when transmission or non-transmission is carried out. The charging portion 119 is, for example, compatible to at least one Universal Serial Bus (USB) charging specification.

Referring to FIG. 3B, the sensing device 110 of an embodiment of the invention includes a processor 310, a sensor 320 coupled to the processor 310, a communication chip 330, a display 340, a battery 350 and an input output element 360. The sensor 320 is, for example, a sensing head constructed by the microphone 114 and the soft cushion ring 115 of the first portion 111. The sensor 320 may further include a start button (not shown). When the patient presses the start button, the sensor 320 starts to measure the physiological data and automatically stops measuring after, for example, five to ten seconds.

Referring to FIG. 1, FIG. 2B and FIG. 3A, in an embodiment, the sensing device 110 contacts a first location 210 of the patient body 105, where there is a first distance D between the first location 210 and a second location 220 of the AVF 203 of the patient body 105, and the first location 210 is located on an extended path of the artery 201 or the vein 202 corresponding to the AVF 203. The sensing device 110 receives a frequency spectrum signal through the microphone 114 and transmits the frequency spectrum signal to the server 130. The server 130 calculates a stenosis percentage of the AVF 203 corresponding to the frequency spectrum signal through a machine learning module and transmits the stenosis percentage to the sensing device 110. Through the machine learning module, the server 130 may determine that the AVF 203 is in a normal state, for example, the stenosis percentage is equal to 0% through a frequency spectrum signal of a normal AVF, for example, the frequency spectrum signal of FIG. 4A. On the other hand, the server 130 may also determine that the AVF 203 is in a stenosis state, for example, the stenosis percentage is equal to 80% through a frequency spectrum signal of an AVF with a severe stenosis condition, for example, the frequency spectrum signal of FIG. 4B.

In an embodiment, the machine learning module performs a training operation by using the frequency spectrum signal corresponding to a plurality of different contact locations between the microphone 114 and the patient body 105, and calculates the stenosis percentage according to a result of the training operation. To be specific, the frequency spectrum signal is a corresponding sound signal. The sound signal has a resonance characteristic in a blood vessel. Even if the contact location between the microphone 114 and the patient body 105 is not on the AVF 203, as long as the patient places the microphone 114 on the extended path of the artery 201 or the vein 202 corresponding to the AVF 203, the microphone 114 may sense the frequency spectrum signal corresponding to the AVF 203. By inputting the frequency spectrum signals corresponding to different locations of the microphones 114 to the machine learning module, a precise prediction result of the stenosis percentage of the AVF 203 may be obtained.

In an embodiment, the server 130 receives angiography information of the patient body 105 and determines a real stenosis percentage according to the angiography information, and the machine learning module trains a plurality of parameters according to the real stenosis percentage to correct the stenosis percentage. In this way, the server 130 may use the exact data of the patient's body 105 to correct the prediction result of the machine learning module, and provide machine learning module to make more accurate prediction of the patient's stenosis percentage.

Figure 5B:
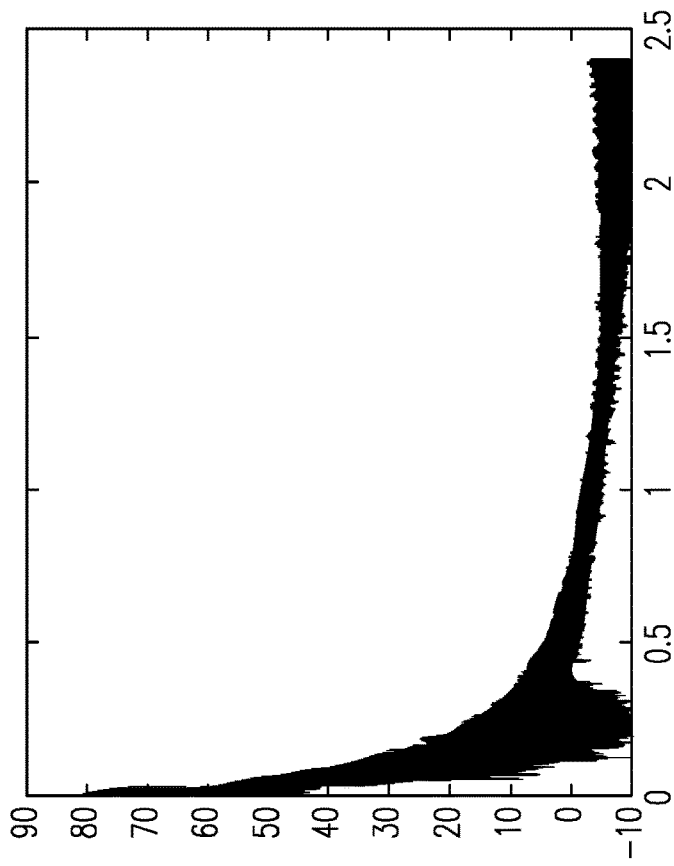
FIG. 5B is a schematic diagram of frequency spectrum energy of an AVF before surgery according to an embodiment of the invention.
Figure 5A:
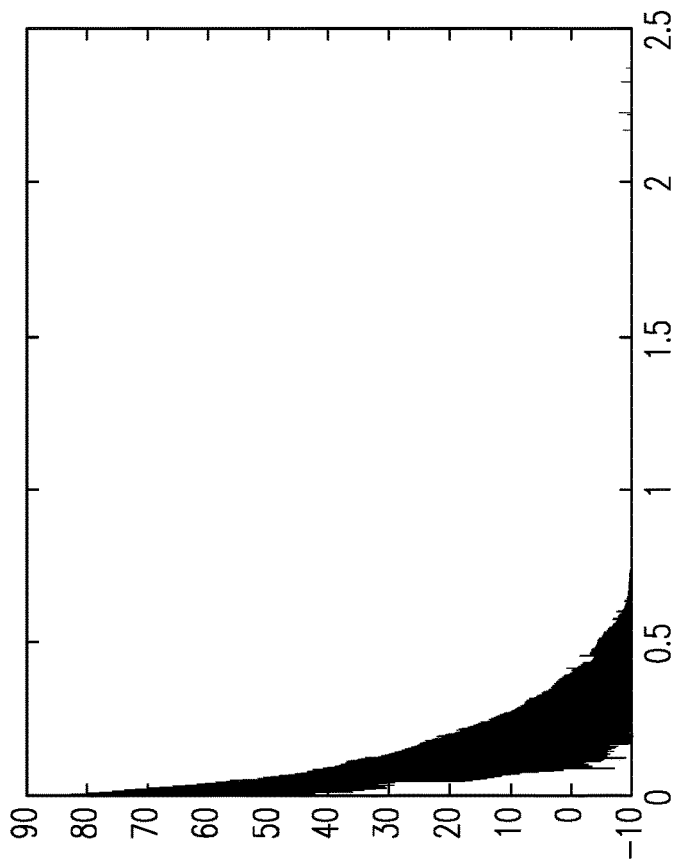
FIG. 5A is a schematic diagram of frequency spectrum energy of an AVF after surgery according to an embodiment of the invention.

FIG. 5A is a schematic diagram of frequency spectrum energy of the AVF after surgery according to an embodiment of the invention. FIG. 5B is a schematic diagram of frequency spectrum energy of the AVF before surgery according to an embodiment of the invention.

Referring to FIG. 5A and FIG. 5B, in the FIG. 5A and FIG. 5B, a horizontal axis represents frequency and a unit there of is Hertz, and a vertical axis represents energy, and a unit thereof is dB. According to FIG. 5B, it is clearly known that the AVF has high frequency energy before surgery, and according to FIG. 5A, it is obvious that the AVF does not have the high frequency energy after the surgery.

Figure 6:
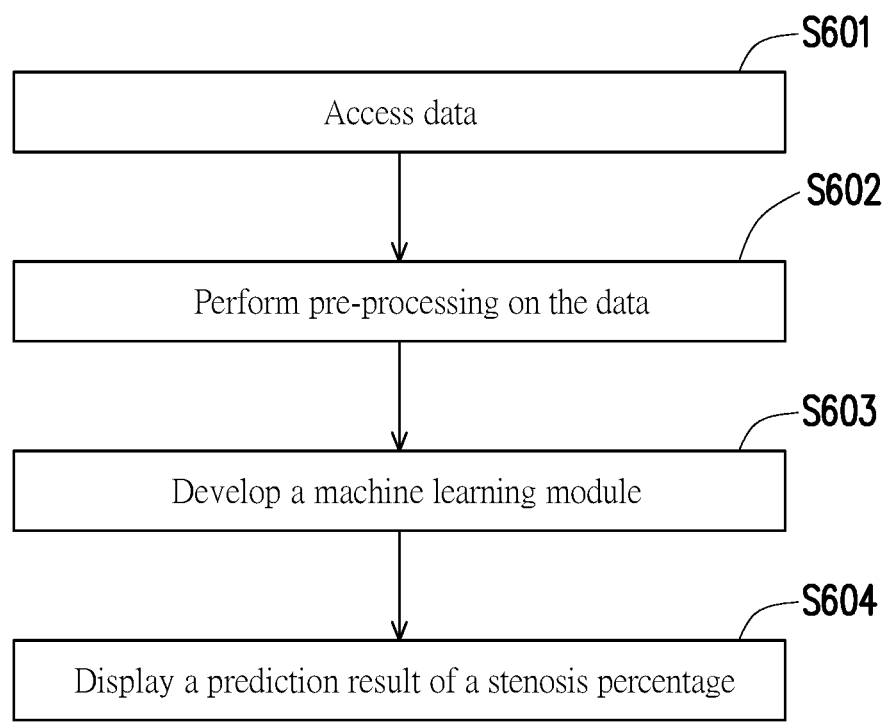
FIG. 6 is a flowchart of machine learning according to an embodiment of the invention.

FIG. 6 is a flowchart of machine learning according to an embodiment of the invention.

Referring to FIG. 6, in a step S601, data is accessed. To be specific, the sensing device 110 may obtain the physiological data from the patient body 105, and the physiological data is, for example, a frequency spectrum signal.

In a step S602, the data is pre-processed. To be specific, the server 130 may receive the frequency spectrum data from the sensing device 110, and transform the frequency spectrum data of raw data into a data format suitable for machine learning.

In a step S603, the machine learning module is developed. To be specific, the machine learning module may first obtain a plurality of influencing parameters, for example, at least one of age information, gender information, blood pressure information, left or right hand, patient historic data, and big data of the server 130. Then, the machine learning module performs feature extraction, parameter optimization, cross comparison, etc., on the format-transformed frequency spectrum data.

In a step S604, a prediction result of a stenosis percentage is displayed. To be specific, after the machine learning module is established, as long as the server 130 receives one batch of frequency spectrum data, the server 130 may generate a corresponding stenosis percentage. The server 130 may send a notification corresponding to the stenosis percentage to display the stenosis percentage on the mobile device 120 and/or the sensing device 110 by ways of email, message or visualization.

In summary, in the AVF stenosis detection system, the method thereof and the sensing device of the invention, the sensing device contacts any location on the extended path of the artery or the vein corresponding to the AVF to receive the frequency spectrum signal and transmits the frequency spectrum signal to the server. The server calculates the stenosis percentage of the AVF corresponding to the frequency spectrum signal and transmits the stenosis percentage to the sensing device. The machine learning module further performs a training operation according to a frequency spectrum signal obtained when the sensing device contacts a different location of the patient body, and calculates the stenosis percentage according to a result of the training operation. Moreover, the server may also receive angiography information of the patient body and determines a real stenosis percentage according to the angiography information, and the machine learning module trains a plurality of parameters according to the real stenosis percentage to correct the stenosis percentage.

It will be apparent to those skilled in the art that various modifications and variations can be made to the disclosed embodiments without departing from the scope or spirit of the invention. In view of the foregoing, it is intended that the invention covers modifications and variations provided they fall within the scope of the following claims and their equivalents.

What is claimed is:

1. An arteriovenous fistula stenosis detection system, comprising:
   a sensing device, comprising:
      a microphone, configured to be disposed at a first location of a patient, and configured to receive a sound signal and convert the sound signal to a frequency spectrum signal, wherein the first location is located on an extended path of an artery or a vein corresponding to an arteriovenous fistula located at a second location on the patient, and the first location and the second location are separated by a first distance; and
   a server, coupled to the sensing device, configured to receive the frequency spectrum signal from the sensing device, determine a stenosis state of the arteriovenous fistula on the extended path of the artery or the vein corresponding to the arteriovenous fistula by using the received frequency spectrum signal as input to a machine learning model, wherein the machine learning model calculates an estimated stenosis percentage of the arteriovenous fistula, and transmits the estimated stenosis percentage calculated by the machine learning model to the sensing device or a mobile device,
   wherein the machine learning model is trained by using a plurality of training frequency spectrum signals and an angiography information corresponding to the training frequency spectrum signals, wherein the angiography information indicates real arteriovenous fistula stenosis condition, and each of the training frequency spectrum signals is respectively obtained from a plurality of training locations, and each of the training locations is different from each other.

2. The arteriovenous fistula stenosis detection system as claimed in claim 1, wherein the microphone is coupled to a confined space of the sensing device.

3. The arteriovenous fistula stenosis detection system as claimed in claim 1, wherein the machine learning module trains a plurality of parameters based on the frequency spectrum signals, the angiography information corresponding to the frequency spectrum signals, and at least one of age information, gender information, blood pressure information, the same second location and patient historic data.

4. The arteriovenous fistula stenosis detection system as claimed in claim 1, wherein the machine learning model is trained by using a plurality of correspondence pairs respectively collected from a plurality of patients, and each correspondence pair includes the plurality of training frequency spectrum signals and the angiography information corresponding to the training frequency spectrum signals that are collected from different patients among the plurality of patients.

5. A method for detecting arteriovenous fistula stenosis, comprising:

disposing a microphone of a sensing device at a first location of a patient, and receiving receive a sound signal, wherein the first location is located on an extended path of an artery or a vein corresponding to an arteriovenous fistula located at a second location on the patient, and the first location and the second location are separated by a first distance;

converting the sound signal to a frequency spectrum signal;

receiving, by a server, the frequency spectrum signal from the sensing device; and determining, by the server, a stenosis state of the arteriovenous fistula on the extended path of the artery or the vein corresponding to the arteriovenous fistula by using the received frequency spectrum signal as input to a machine learning model, wherein the machine learning model calculates an estimated stenosis percentage of the arteriovenous fistula, and transmits the estimated stenosis percentage calculated by the machine learning model to the sensing device or a mobile device, wherein the machine learning model is trained by using a plurality of training frequency spectrum signals and an angiography information corresponding to the training frequency spectrum signals, wherein the angiography information indicates real arteriovenous fistula stenosis condition, and each of the training frequency spectrum signals is respectively obtained from a plurality of training locations, and each of the training locations is different from each other.

6. The method for detecting arteriovenous fistula stenosis as claimed in claim 5, wherein the microphone is coupled to a confined space of the sensing device.

7. The method for detecting arteriovenous fistula stenosis as claimed in claim 5, wherein the machine learning module trains a plurality of parameters based on the frequency spectrum signals, the angiography information corresponding to the frequency spectrum signals, and at least one of age information, gender information, blood pressure information, the same second location and patient historic data.

\* \* \* \* \*